US00PP33976P2

(12) United States Plant Patent
Vinson

(10) Patent No.: US PP33,976 P2
(45) Date of Patent: Mar. 1, 2022

(54) ***FRAGARIA* PLANT NAMED 'SRE36'**

(50) Latin Name: ***Fragaria* x *ananassa***
Varietal Denomination: SRE36

(71) Applicant: Edward Vinson Ltd., Kent (GB)

(72) Inventor: Peter Edward Vinson, Kent (GB)

(73) Assignee: EDWARD VINSON LTD., Faversham (GB)

( * ) Notice: Subject to any disclaimer, the term of this patent is extended or adjusted under 35 U.S.C. 154(b) by 0 days.

(21) Appl. No.: 17/072,195

(22) Filed: Oct. 16, 2020

(51) Int. Cl.
*A01H 5/08* (2018.01)
*A01H 6/74* (2018.01)

(52) U.S. Cl.
USPC ..... Plt./208

(58) Field of Classification Search
USPC ..... Plt./208
CPC ... A01H 5/08; A01H 5/00; A01H 6/74; A01H 6/7409
See application file for complete search history.

(56) References Cited

PUBLICATIONS

Google translate from Spanish to English of foreign document retrieved on Apr. 27, 2021, 2 pp. (Year: 2021).*
Upov Pluto Plant Variety Database 20200427, retrieved on Apr. 27, 2021, retrieved from the Internet at https://www.upov.int/pluto/en/index.jsp, 2pp. (Year: 2021).*

* cited by examiner

*Primary Examiner* — June Hwu
(74) *Attorney, Agent, or Firm* — Penny J. Aguirre

(57) ABSTRACT

A new and distinct Mediterranean short-day cultivar of strawberry plant named 'SRE36' that is characterized by its uniformly medium to large and conical shaped berries, its berries that are consistently glossy and orange-red in color, its sweet tasting berries that are high in sugar and low in acid, its vigorous and compact growth habit with dark green leaves, and its substantial fruit yields of marketable quality that is medium-late in season.

2 Drawing Sheets

Botanical classification: *Fragaria* x *ananassa.*
Variety denomination: 'SRE36'.

BACKGROUND OF THE INVENTION

The present invention relates to a new and distinct cultivar of *Fragaria*, botanically known as *Fragaria* x *ananassa* and will be referred to hereafter by its cultivar name, 'SRE36'. 'SRE36' is a Mediterranean short-day strawberry plant primarily adapted to the climate and growing conditions of the Mediterranean and other regions of similar climate and day length and used for the fresh fruit market.

The new cultivar was derived from an ongoing breeding program conducted by the Inventor in Cartaya, Huelva, Spain and Faversham, Kent, United Kingdom. 'SRE36' arose from a controlled cross made by the Inventor in 2012 in Faversham, Kent, United Kingdom between an unnamed and unpatented selection from the Inventor's breeding program, designated as accession number 'SVP05' as the female parent and an unpatented selection from the Inventor's breeding program, designated as accession number 'SYB82' as the male parent. 'SRE36' was selected as a single unique plant in the spring of 2013 from amongst the seedlings that resulted from the above cross in Cartaya, Huelva, Spain.

Asexual reproduction of the new cultivar was first accomplished by rooting of stolons by the Inventor in Faversham, Kent, United Kingdom in 2013. Asexual propagation by rooting of stolons and tissue culture using meristematic tissue has shown that the unique characteristics of the new cultivar are stable and reproduced true to type in successive generations.

BRIEF SUMMARY OF THE INVENTION

The following traits have been repeatedly observed and represent the characteristics of the new cultivar. These attributes in combination distinguish 'SRE36' as a new and unique cultivar of *Fragaria.*

1. 'SRE36' exhibits a semi-upright growth habit.
2. 'SRE36' exhibits uniformly medium to large and conical shaped berries.
3. 'SRE36' produces berries that are consistently glossy and orange-red in color.
4. 'SRE36' produces sweet tasting berries that are high in sugar and low in acid.
5. 'SRE36' exhibits a vigorous and compact growth habit with dark green leaves.
6. 'SRE36' produces substantial fruit yields of marketable quality that is medium-late in season.

'SVP05', the female parent of 'SRE36', differs from 'SRE36' in having berries that have a lower sugar content, a more complex truss architecture and an increased predisposition to brown coloration on the calyx. 'SYB82', the male parent of 'SRE36', differs from 'SRE36' in having a smaller fruit size, a less uniformly conical shape and a darker berry coloration.

'SRE36' can most closely be compared to the cultivar 'SSL 93' (U.S. Plant Pat. No. 26,874) with the following comparison characteristics being observed under growing conditions in Huelva, Spain. 'SRE36' produces on average much larger fruit across the whole season than 'SSL 93' with a similar conical shape. 'SRE36' exhibits a comparable berry evenness and therefore has a similar percentage of class I fruit compared to 'SSL 93'. However, 'SRE36' has a higher total yield across the whole season, so the total weight of class I fruit is greater for 'SRE36'. The skin firmness of the 'SRE36' berry is generally quite similar to 'SSL 93', while the flesh firmness is significantly softer for 'SSL 93'. 'SRE36' also has a shorter average truss length than 'SSL 93' with both varieties exhibiting a mostly outward calyx position relative to the fruit.

The plant vigor of 'SRE36' and 'SSL 93' differs in multiple ways. 'SRE36' is generally shorter than 'SSL 93', has a more compact and denser canopy with a generally smaller leaf size. While the petiolule lengths are similar between 'SRE36' and 'SSL 93', the petiole length is considerably shorter in 'SRE36' which leads to the more compact plant architecture. The petiole pubescence is generally stronger in 'SSL 93' when compared to 'SRE36' but the petiolule pubescence manifests as moderate in both varieties. Both petiole and petiolule widths are slightly greater in 'SSL 93' when compared to 'SRE36'.

The shape of the leaves for both varieties can be described as round with the length and width being relatively equal. The base and apex are obtuse and rounded respectively for both 'SRE36' and 'SSL 93'. On average, 'SRE36' has more serrations per leaf than 'SSL 93' however both can be defined as serrate to crenate in their appearance. In cross section, the majority of leaves for both 'SRE36' and 'SSL 93' are concave in their aspect. However, they differ in relation to blistering on the leaf surface, which is far less prominent in 'SRE36' compared to 'SSL 93'. The coloration of the leaves can be used to distinguish between the two varieties too, with 'SRE36' leaves expressing as a darker shade of green when compared to 'SSL 93'. The leaf surface of 'SRE36' also appears to be glossier than 'SSL 93'.

Despite a considerably longer truss length in 'SSL 93' than 'SRE36', both varieties display their inflorescences in a similar way with the majority presented level with the plant canopy. The flowers of 'SSL 93' express themselves earlier than 'SRE36'.

On average, the corolla size is smaller in 'SRE36' than in 'SSL 93. Despite this, the calyx of 'SSL 93' is often larger than the corolla whereas in 'SRE36' the calyx and corolla are usually a similar size. Both display a petal shape of a rounded base and apex with fewer petals on average in 'SRE36' compared to 'SSL 93'. In general, petals of 'SRE36' are longer than they are wide whereas in 'SSL 93' the petals usually have a greater width compared to their length. In both varieties, the arrangement of petals overlap one another.

While 'SRE36' has a calyx that is generally flat to slightly recurved relative to the fruit, the calyx of 'SSL 93' is mostly recurved. The calyx generally sits level with the shoulder of the fruit in both varieties, with both 'SRE36' and 'SSL 93' producing a calyx that usually has a greater diameter relative to the fruit width. This greater calyx width is especially apparent at the start of the season.

On average, the berry size of 'SRE36' is larger than that of 'SSL 93' with similar fruit shape uniformity observed between the two varieties; both varieties exhibit conical shaped berries that are glossy. While the color of both varieties is uniformly maintained throughout the season, the fruit of 'SRE36' is a paler shade of red than 'SSL 93'. The number of achenes is generally greater in 'SRE36' compared to 'SSL 93' but the achene position is level with the fruit surface for both varieties.

Both 'SRE 36' and 'SSL 93' produce berries that are high in Brix and reasonably low in acidity. The skin firmness of 'SRE36' is similar to that of 'SSL 93' with the berries of 'SSL 93' also perceived to be juicier than 'SRE36'.

BRIEF DESCRIPTION OF THE DRAWINGS

The accompanying colored photographs illustrate the overall appearance and distinct characteristics of the new cultivar. The photographs were taken of five-month-old plants of 'SRE36' as grown in trial fields with tunnels and polyethylene covers in Cartaya, Huelva, Spain. The photographs depict color features as true as reasonably possible with the digital photography methods used.

The photograph in FIG. 1 provides a view of a fruiting plant of 'SRE36'.

Figure 1:
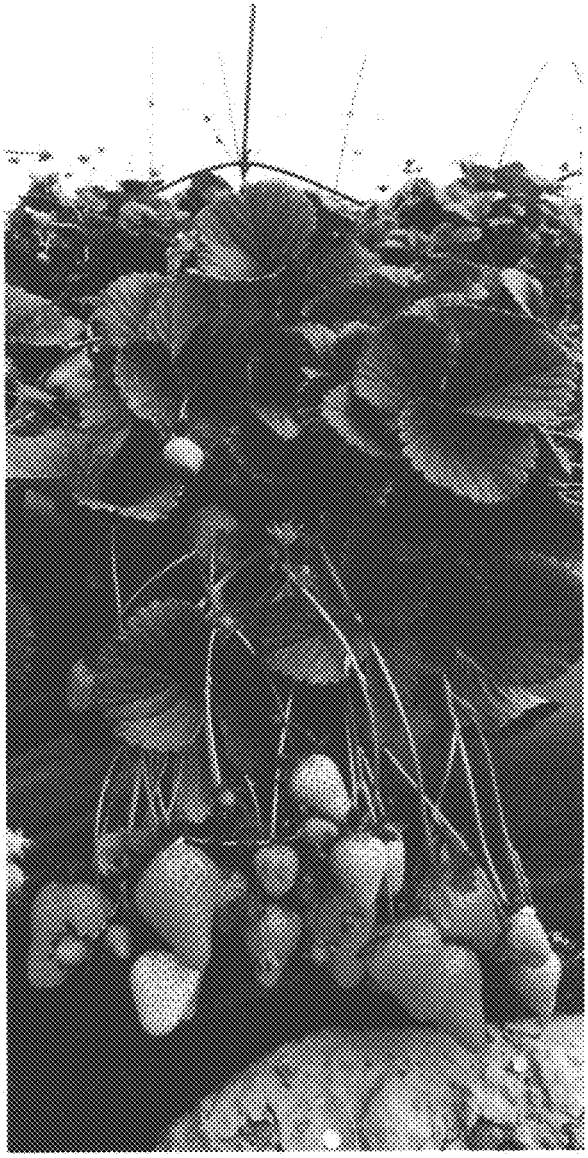
Figure 2:
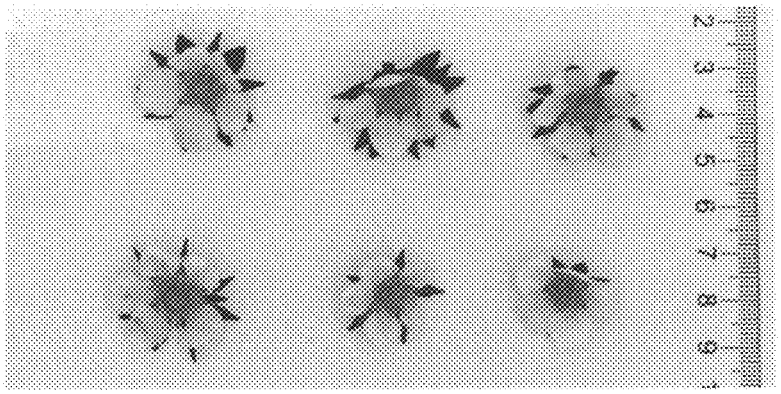

The photograph in FIG. 2 provides a view of the upper surface of the flowers of 'SRE36'.

Figure 3:
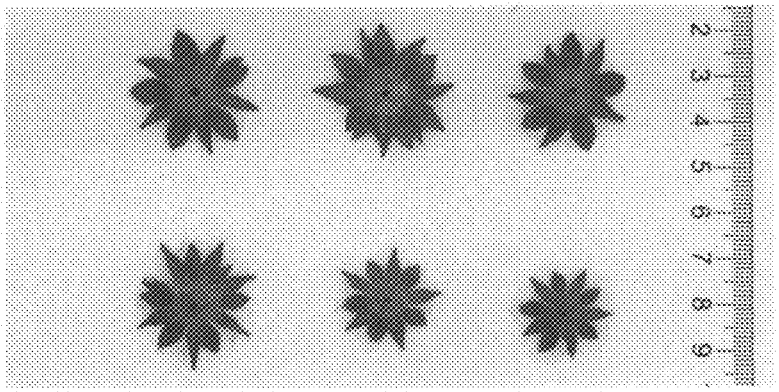

The photograph in FIG. 3 provides a view of the lower surface of the flowers of 'SRE36'.

Figure 4:
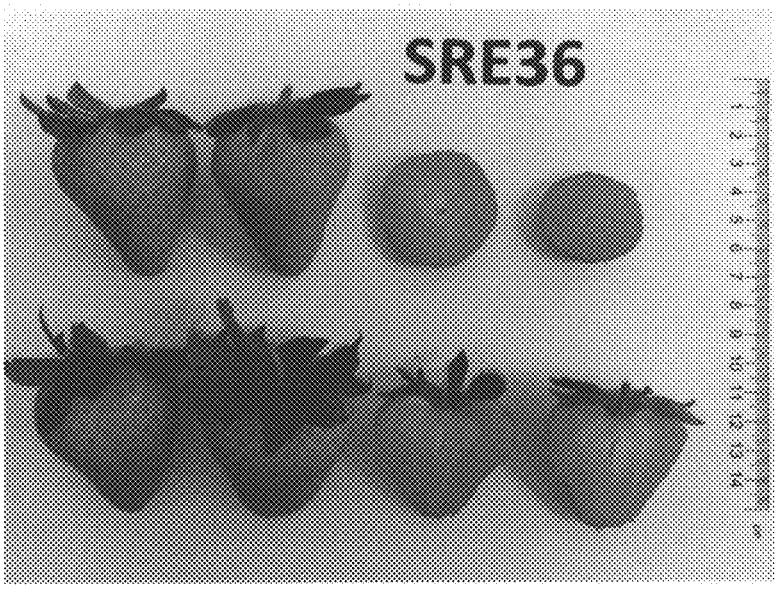

The photograph in FIG. 4 provides a close-up view of the fruit of 'SRE36'.

DETAILED BOTANICAL DESCRIPTION

The following is a detailed description of plants five months after planting a bare rooted plant of 'SRE36' as grown in the soil, in raised beds, under tunnels with polyethylene covers in Cartaya, Huelva, Spain. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Mid-January through Mid-May in Cartaya, Huelva, Spain.

*Plant type.*—Herbaceous fruit producing perennial.

*Plant habit.*—Semi-upright, compact with dense canopy.

*Height and spread.*—Medium-large; reaches an average of 25.6 cm in height and 46.2 cm in width with an average height to width ratio of about 5:9.

*Crown diameter.*—Average total diameter of 5.3 cm with an average crown number of about 5.

*Cold hardiness.*—Not tested in areas where temperatures of less than 32° F. occur.

*Diseases and pests.*—No susceptibility to disease or pests has been observed under the trial conditions.

*Root description.*—Fibrous, white in color.

*Root development.*—An average of 2 weeks to initiate roots and 5 weeks to produce a young rooted plant.

*Propagation.*—Rooting of stolons and tissue culture.

*Growth rate.*—Moderately vigorous.

*Stem description.*—Acaulescent.

*Stolons.*—Average of 7 during the fruiting season, an average of 52 cm in length, color 145B on initial growth and 145A on mature growth, medium anthocyanin coloration, medium density of pubescence.

Foliage description:

*Leaf division.*—Three leaflets.

*Leaf arrangement.*—Basal.

*Leaf attachment.*—Petiolate.

*Leaflet shape.*—Rounded.

*Leaves per plant.*—Average 31.4 trifoliate leaves.

*Terminal leaflet size.*—Average of 6.3 cm in length and 6.5 cm in width; an average length to width ratio of 1:1.

*Leaflet margins.*—Serrate to crenate, an average of 23.2 serrations per leaf.

*Leaflet base.*—Acute.

*Leaflet apex.*—Round.

*Leaflet glossiness.*—Upper surface medium to strong, lower surface dull.

*Leaflet aspect.*—Mostly concave.

*Leaflet interveinal blistering.*—Weak.

*Leaflet venation.*—Pinnate, coloration matches leaflet color.

*Leaflet surface.*—Upper surface glabrous, lower surface very slightly pubescent but strongly pubescent along the vein.

*Leaflet color.*—Upper surface NN137A, lower surface 191A, no variegation present on either surface.

*Petiole.*—Round in shape, average of 11.7 cm in length and 4.0 mm in width, 145A in color, moderately to strongly pubescent surface with most hairs horizontal in attitude.

*Petiolules.*—Round in shape, average of 1.01 cm in length and 2.1 mm in width, moderately to strongly pubescent surface with most hairs horizontal in attitude, 145A in color.

*Stipule.*—Average of 3.07 cm in length, 2.07 cm in width with absent/very weak anthocyanin coloration, 145A in color with edges blending to NN155C.

Flower description:

*Inflorescence type.*—Truss.

*Inflorescence size.*—Average of 8.99 cm in length before branching and 3.4 mm in width.

*Inflorescence no.*—Average of 11 trusses per plant.

*Flower initiation and expression conditions.*—Temperature and day length dependent.

*Time of flowering* (50% *of plants at first flower*).—Mid to late season.

*Flower position relative to foliage.*—Mostly level with the leaf canopy.

*Corolla size in relation to calyx.*—Mostly same size.

*Flower number per truss.*—Average 3.5, more flowers per truss later in season.

*Flower size.*—Average of 2.9 cm diameter and 5.8 mm depth.

*Flower fragrance.*—Weak.

*Calyx.*—Average of 3.78 cm in diameter at the start of the season, dropping to 2.6 cm nearer the end of the season.

*Sepals.*—Average of 11 per flower, oblong to oblanceolate with an obtuse base and an acute apex, average of 1.49 cm in length and 7.5 mm in width at the start of the season, 9.7 mm in length and 3.9 mm in width nearer the end of the season, the adaxial color most closely resembles 141B while the abaxial color most closely resembles 138B, pubescence is medium on abaxial surface and weak on the adaxial surface, aspect is flat on both surfaces.

*Sepal position.*—Mixed arrangement relative to the fruit, most horizontal with fruit shoulder and some recurved upwards.

*Petals.*—5 to 6 in number, average of 1.58 cm in length and 1.46 cm in width, an average length to width ratio of 1.1:1, rounded in shape, obtuse base and apex, mostly overlapping in their arrangement, entire margins, upper and lower surface glabrous and in color.

*Peduncle.*—145B color, moderate in strength, moderate to strong pubescence with a generally horizonal hair attitude, average of 8.99 cm in length and 3.4 mm in width.

*Pedicel.*—145B color, moderate to strong pubescence with a generally horizontal hair attitude, average of 5.53 cm in length from peduncle to terminal fruit and 1.7 mm in width.

*Bracts.*—Observed on most flower trusses from early developmental stage, which progresses into a small single leaflet as the truss matures and fruit develops, characteristics similar to leaflets.

Reproductive organs:

*Gynoecium.*—Average of 7.3 mm in width and 5.8 mm in height, steeply dome shaped, multiple simple pistils present with capitate shaped stigma 2A in color.

*Androecium.*—Stamens; average of 26 per flower, 3.3 mm in length, 0.3 mm in diameter at the midpoint, shape is a cone-like tube and wider at the base, anther; oval in shape, average of 1.0 mm in length, 12A in color, pollen; moderate in quantity.

Fruit description:

*Shape.*—Predominantly conical. Shape is similar for primary, secondary and tertiary fruit.

*Season of harvest.*—Late February through to May in Cartaya, Huelva, Spain.

*Time of ripening* (50% *of plants with first ripe fruit*) .—Medium-late.

*Type of bearing.*—Short-day Mediterranean.

*Size.*—Medium to large; an average of 5.46 cm in length and 4.36 cm in width, an average length to width ratio of 1.3:1.

*Surface.*—Smooth and medium glossy.

*Calyx position.*—Mostly level with fruit and horizontal with some re-curved.

*Attitude of calyx segments.*—Mostly outwards with some re-curved. Strongly adhered to the fruit.

*Diameter of calyx relative to fruit diameter.*—Calyx is usually slightly larger than fruit diameter.

*Glossiness.*—Even with medium to strong gloss.

*External color* (*skin*).—33A, color is retained throughout the cropping season.

*Internal color* (*flesh*).—Near skin; 31A, near center; 31B, core N155D.

*Evenness of color of skin.*—Very even.

*Evenness of color of flesh.*—Paler near center.

*Acidity.*—Low, total titratable acid of 0.44 g/L.

*Sweetness.*—High.

*Soluble solids.*—Average of 7.7°.

*Firmness.*—Skin is moderately firm, flesh is firm.

*Juiciness.*—Moderate.

*Aroma.*—Slight.

*Weight.*—Average of 27.3 g per berry and 1172 g per plant over three seasons in trials.

*Number of fruit per plant.*—Average 43 over three seasons in trials.

*Fruit cavity.*—Small; an average of 2.57 cm in length and 6.6 mm in width with a length to width ratio of 4:1, generally more prominent on primary fruit.

*Shipping quality.*—Good, has been observed to exceed 5 days when subjected to usual supply chain conditions.

*Achene color.*—Mostly 150A.

*Achene position.*—Majority level with surface.

*Achene number.*—An average of 350 per berry.

*Band without achenes.*—Absent or very narrow.

It is claimed:

1. A new and distinct cultivar of *Fragaria* plant named 'SRE36' as herein illustrated and described.

* * * * *